United States Patent [19]

Bergersen

[11] Patent Number: 5,037,295
[45] Date of Patent: Aug. 6, 1991

[54] MUSCULAR EXPANSION ORAL SHIELD APPLIANCE

[76] Inventor: Earl O. Bergersen, 950 Green Bay Rd., Winnetka, Ill. 60093

[21] Appl. No.: 436,756

[22] Filed: Nov. 15, 1989

[51] Int. Cl.$^5$ .............................................. A61C 3/00
[52] U.S. Cl. ............................................ 433/6; 433/7
[58] Field of Search ...................... 433/6, 7; 128/861

[56] References Cited

U.S. PATENT DOCUMENTS

| | | | |
|---|---|---|---|
| 2,789,351 | 4/1957 | Gordon | 433/6 |
| 3,286,576 | 11/1966 | West | 433/6 |
| 3,327,580 | 6/1967 | Herweg | 433/6 |
| 3,478,429 | 11/1969 | Shilliday | 433/6 |
| 3,478,742 | 11/1969 | Bohlmann | 433/6 |
| 4,055,895 | 11/1977 | Huge | 433/6 |
| 4,512,740 | 4/1985 | Kurz | 433/6 |
| 4,764,112 | 8/1988 | Bergersen | 433/5 |
| 4,784,605 | 11/1988 | Bergersen | 433/6 |
| 4,797,093 | 1/1989 | Bergersen | 433/5 |
| 4,799,884 | 1/1989 | Bergersen | 433/6 |
| 4,856,992 | 8/1989 | Bergersen | 433/18 |
| 4,881,896 | 11/1989 | Bergersen | 433/5 |
| 4,898,535 | 2/1990 | Bergersen | 433/6 |

FOREIGN PATENT DOCUMENTS 371930  4/1973  U.S.S.R. .................. 433/6

*Primary Examiner*—Gene Mancene
*Assistant Examiner*—Michael Lynch
*Attorney, Agent, or Firm*—Hill, Van Santen, Steadman & Simpson

[57] ABSTRACT

A muscular expansion oral shield appliance having a buccal shield supported laterally and anteriorly away from the expansion appliance to engage the buccal musculature. The shield may be formed integrally with the appliance or may be mounted thereto in a permanent manner such as by a wire or wires secured to the appliance and the shield or may be mounted thereto in a removable manner such as with a ball and socket type attachment.

18 Claims, 1 Drawing Sheet

MUSCULAR EXPANSION ORAL SHIELD APPLIANCE

BACKGROUND OF THE INVENTION

1. Field of the Invention

The present invention relates to orthodontic appliances and more particularly to an appliance for assisting in lateral expansion of the upper and/or lower posterior segments.

2. Description of the Prior Art

Overcrowding of the teeth, particularly the anterior teeth is one condition which can be corrected with orthodontic treatment. Oftentimes metallic bands and wires are used in the permanent dentition stage to provide a desired spacing. There have also been provided devices such as my prior device disclosed in U.S. Pat. No. 4,139,944 in which a plastic movable positioner is provided for use in correcting certain conditions in a permanent or mixed dentition stage.

It is known in various applications to use a buccal shield to hold the buccal musculature away from the teeth so as to remove pressure against the teeth in the buccal to lingual direction.

SUMMARY OF THE INVENTION

The present invention provides a bi-lateral buccal shield with a thinner portion extending around the anterior labial area of the teeth in the sulcus between the alveolar bone and the lips in the muco-buccal fold. This would allow the patient to open and close the mouth and still maintain the "lifting away" of the buccal musculature from the teeth during speech and eating.

The appliance can be relatively hard across the front covered with a softer material or it can have a wire embedded in this labial section covered with soft plastic that could be bent and adapted to the tissues of the mouth to prevent abrasion of the plastic against the tissues either labially or buccally.

The buccal shield would simply expand the posterior segments laterally and could be worn all the time as a primary appliance or as an expansion day or night part-time appliance when less expansion would be necessary. Both kinds may or may not have an anterior tooth bearing area. The appliance preferably is preformed in several sizes to accommodate different sized mouths (or teeth) and would be coordinated in size with the expansion appliance with an anterior tooth bearing area.

The appliance could be made of several types of plastics, hard or soft, and could also be made of a thermal variable plastic where it could be softened in a range of, for example, 120° to 212° F. and adapted to the mouth.

In an embedded wire version, the wire within the buccal shield would preferably be bent in a wave form to prevent the buccal shield from twisting around on the wire. The buccal shield could also be torqued on itself to slant the shield from buccal to lingual as well as up and down. In this way, the buccal shield could be widened to expand both upper and lower posterior segments or to expand only the upper or lower posterior segment, or to expand one side individually over the other. The appliance could have one or more labial cross beams across the labial of the mouth for support or a single beam with a large breathing hole or several breathing holes in the middle in the front of the mouth, or the wire can cross over from the buccal posterior to the lingual of the incisors. The cross over could be made in the embrasure between the canines and lateral incisor or between any two teeth.

DESCRIPTION OF THE PREFERRED EMBODIMENTS

In FIGS. 1-5 there is illustrated a muscular expansion oral shield appliance generally at 10 which includes a bi-lateral buccal shield 12 as part of and incorporated into an expansion appliance 14. The expansion appliance 14 can be similar to those previously disclosed in my U.S. Pat. Nos. 3,939,598; 3,898,736 and 4,073,061 with the exception that the lingual posterior upper and lower flanges have been removed and the occlusal isthmus has been slightly shortened on the lingual. The disclosures of these patents are fully incorporated herein by reference.

Figures 4, 5:
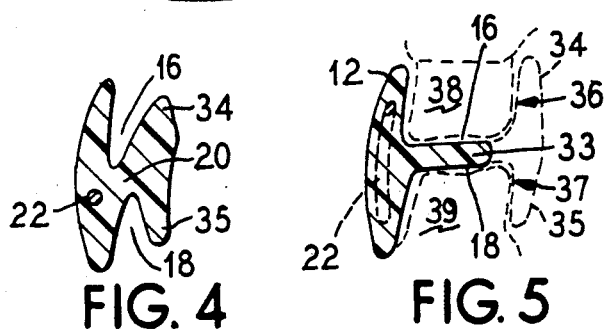
FIG. 4 is a sectional view taken generally along the line IV—IV of FIG. 2.
FIG. 5 is a side sectional view taken generally along the line V—V of FIG. 2.

Generally, the expansion appliance comprises at least one of an upper tooth receiving trough 16 and a lower tooth receiving trough 18 separated by a central web or isthmus 20. The appliance is designed and fitted so as to urge the posterior teeth at least laterally and perhaps distally. The posterior segment, as illustrated in FIG. 5, has a shortened central web 33, while lingual flanges 34 and 35 have been removed so lateral pressure at arrows 36 and 37 is exerted by the tongue to move the posterior teeth 38 and 39 to the buccal since the buccal shield 12 has been expanded away from the teeth 38 and 39.

The buccal shield 12 can be expanded laterally from the teeth 38 and 39 and the shield 12 is held in this spaced relationship by means of a wire 22 which is molded into the expansion appliance 14 and also is molded within the shield 12. Preferably, the portion of the wire within the shield 12 has a serpentine or wavy form as seen in FIG. 1 so that the buccal shield 12 will not twist on the wire.

Figure 1:
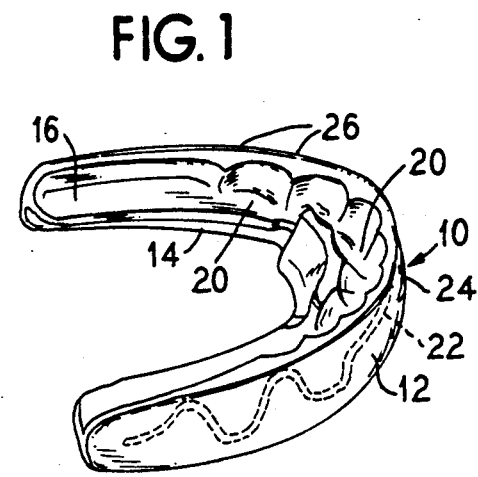
FIG. 1 is a perspective view of an appliance embodying the present invention which includes an expansion appliance with the buccal wire incorporated into the labial and buccal flanges of the appliance and the upper and lower lingual flanges removed so that the pressure from the tongue will push the posterior teeth laterally as the cheek pressure has been removed by the expanded buccal shield.
Figure 3:
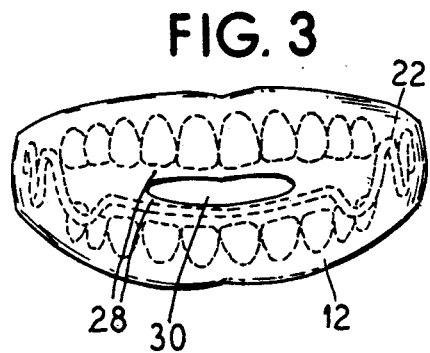
FIG. 3 is a front elevational view of the appliance of FIG. 1.

As illustrated in FIG. 1, the buccal shield 12 has a portion 24 extending around the anterior labial area of the teeth, a buccal portion 26 of the shield extending around the posterior buccal area. The anterior portion 24 could comprise one or more cross beams 28, as illustrated in FIG. 3, to provide lateral support between the buccal shield on either side of the mouth, and if a single beam is used, then a large breathing hole 30 preferably is formed in the middle in the front of the mouth.

With the embedded wire embodiment illustrated in FIGS. 1-5, the buccal shield 12 can be repositioned to slant the shield from buccal to lingual as well as slanting the shield up and down. This provides a measure of customizing the appliance to a particular patient's requirement of expansion. In this way, expansion can be provided in upper or lower or both, on one side or the other or both, or mesially or distally or both.

As seen in FIG. 5, the buccal shield portion 12 is formed integrally with the central web 33 as a single molded piece, while the lingual flanges 34 and 35 of FIG. 4 have been removed distal to the lateral incisors but remain in the anterior segment as seen in FIG. 4. In this way, the incisors remain in place labio-lingually while the teeth from the canines distally can expand bucally. This type of construction, where the central web 33 is slightly shortened and where the lingual flanges 34 and 35 are removed, allows pressure to be exerted by the tongue thereby eliminating complicated fixed appliances designed to exert expansion pressure from the lingual.

Figure 6:
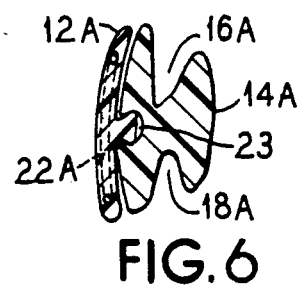
FIG. 6 is a side sectional view of an alternative embodiment of the invention wherein the shield is detachably secured to the expansion appliance.
Figure 7:
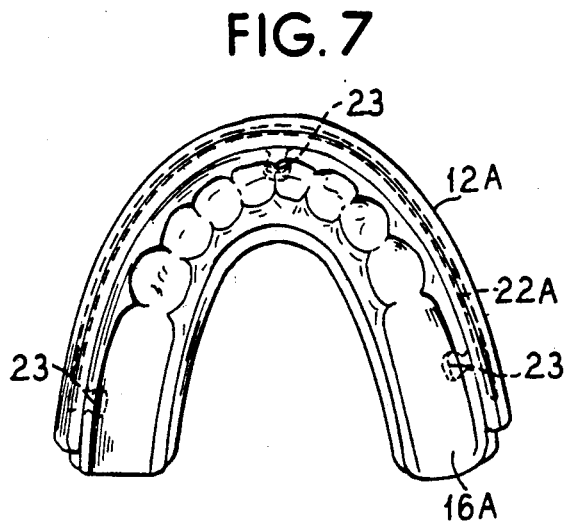
FIG. 7 is an occlusal view of the embodiment illustrated in FIG. 6.

FIGS. 6 and 7 illustrate an alternative embodiment in which a buccal shield portion 12A is detachably secured to an expansion appliance portion 14A. Fastening means 23 are provided between the two parts to permit the selected attachment and detachment. The particular fastening device which is shown is a ball and socket connection although numerous types of connections could be utilized. The buccal shield 12A is formed of two materials, a relatively hard material forming the main body of the shield and a relatively soft material covering the hard material to prevent abrasion of the tissues within the mouth.

Figure 8:
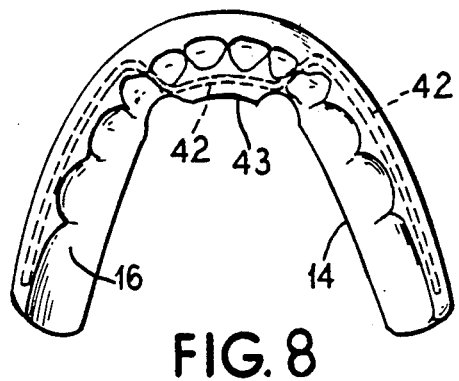
FIG. 8 is an occlusal view illustrating an alternative method of allowing the embedded wire to cross the anterior segment.

FIG. 8 shows an alternative method of getting a wire 42 to cross the anterior segment 43 by crossing over from buccal to lingual in the embrasure between the canine and lateral incisor.

Figure 2:
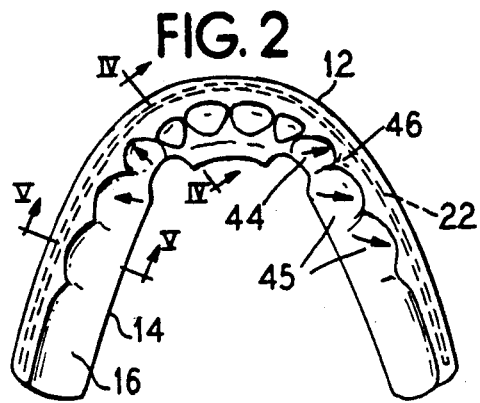
FIG. 2 is an occlusal view of the appliance of FIG. 1.

FIG. 2 also shows how the arrangement of the tooth sockets 44 and 45 encourage the canine and deciduous molar or bicuspid crowns to expand in a distal direction as shown by arrows. This enables additional space to be created distal to the lateral incisors 46.

The wire 22 can also be incorporated into a standard appliance 24 where the central web 33 has not been shortened or the lingual flanges 34 and 35 have not been removed. In this configuration the appliance could simply receive alteration of the wire to enable the appliance to conform more readily to an unusual arch form such as a "V"-shaped or square-type arch.

As is apparent from the foregoing specification, the invention is susceptible of being embodied with various alterations and modifications which may differ particularly from those that have been described in the preceding specification and description, or could be adapted to both preformed or custom-made appliances of various materials such as plastic, rubber, silicone or any other moldable or formable material. It should be understood that I wish to embody within the scope of the patent warranted hereon all such modifications as reasonably and properly come within the scope of my contribution to the art.

I claim as my invention:

1. A muscular expansion oral shield appliance comprising:
   an expansion appliance having at least one of an upper tooth receiving a trough and a lower tooth receiving trough, said trough being formed between a labial-buccal flange and a lingual flange connected by an isthmus to be engaged by the occlusal surfaces of the teeth; and
   a buccal shield held outwardly of said labial-buccal flange to engage an interior surface of the user's lips and cheeks, said buccal shield being held outwardly of said labial-buccal flange by means of a detachable connection between said labial-buccal flange and said shield.

2. A muscular expansion oral shield appliance according to claim 1, wherein said detachable connection comprises a ball member carried on an inwardly directed post secured to an inside surface of the shield and a socket formed in said labial-buccal flange to snappingly receive said ball.

3. A muscular expansion oral shield appliance comprising:
   a bi-lateral buccal shield having a thinner portion to extend around an anterior labial area of the teeth and a pair of thicker portions extending posteriorly of the anterior portion; and
   means for holding said buccal shield away from the teeth and in contact with buccal musculature when the appliance is being worn by a user, said means selected from the group comprising:
   (a) a wire embedded in said means at one portion and in said shield at another portion; and
   (b) a detachable connection.

4. A muscular expansion oral shield appliance according to claim 3, wherein said buccal shield has a labial portion extending around the anterior labial portion of the teeth and a buccal portion extending posteriorly on either side of the labial portion being somewhat thicker than said labial portion.

5. A muscular expansion oral shield appliance according to claim 4, wherein said labial portion comprises at least one cross beam providing lateral support between the posterior portions on either side of the mouth.

6. A muscular expansion oral shield appliance according to claim 5, wherein said cross beam has a central breathing opening therein.

7. A muscular expansion oral shield appliance according to claim 5, wherein said labial portion comprises two spaced cross beams.

8. A muscular expansion oral shield appliance according to claim 3, wherein said buccal shield is formed of two materials, a relatively hard material forming a main body of the shield and a relatively soft material covering the hard material.

9. A muscular expansion oral shield appliance according to claim 3, wherein said means comprises an expansion appliance having at least one tooth receiving trough formed between a labial-buccal flange and a lingual flange, and a support means extending between said labial-buccal flange and said buccal shield.

10. A muscular expansion oral shield appliance according to claim 9, wherein said support means is pliable so as to permit the buccal shield to be slanted with respect to said expansion appliance.

11. A muscular expansion oral shield appliance comprising:
    an expansion appliance having at least one of an upper tooth receiving trough and a lower tooth receiving trough, said trough being formed between a labial-buccal flange and a linqual flange connected by an isthmus to be engaged by the occlusion surfaces of the teeth, said labial-buccal flange including a bi-lateral buccal shield having a thinner portion to extend around an anterior labial area of the teeth and a pair of thicker portions extending posteriorly of the anterior portion said buccal shield being separate from said labial-buccal flange and being secured thereto by means of an integral formation of said appliance and said buccal shield comprising a connecting portion between said labial-buccal flange and said buccal shield, said connected portion being in the form of a continuous web.

12. The muscular expansion oral shield appliance of claim 11, wherein said appliance includes a wire embedded therein that is bent in serpentine fashion to prevent the buccal shield from twisting around on the wire.

13. The muscular expansion oral shield appliance of claim 11, wherein the anterior portion comprises at least one cross beam to provide lateral support between the buccal shield on either side of a mouth.

14. The muscular expansion oral shield appliance of claim 11, wherein a wire is embedded in the appliance so that the buccal shield can be repositioned to slant the shield from buccal to lingual, as well as slanting the shield up and down.

15. A muscular expansion oral shield appliance comprising:

an expansion appliance having at least one of an upper tooth receiving trough and a lower tooth receiving trough, said trough being formed between a labial-buccal flange and a lingual flange connected by an isthmus to be engaged by the occlusion surfaces of the teeth, said labial-buccal flange including a bi-lateral buccal shield having a thinner portion to extend around an anterior labial area of the teeth and a pair of thicker portions extending posteriorly of the anterior portion, said buccal shield being separate from said labial-buccal flange and being connected thereto by means of a detachable connection.

16. The muscular expansion oral shield appliance of claim 15, wherein said appliance includes a wire embedded therein that is bent in serpentine fashion to prevent the buccal shield from twisting around on the wire.

17. The muscular expansion oral shield appliance of claim 15, wherein the anterior portion comprises at least one cross beam to provide lateral support between the buccal shield on either side of a mouth.

18. The muscular expansion oral shield appliance of claim 15, wherein a wire is embedded in the appliance so that the buccal shield can be repositioned to slant the shield from buccal to lingual, as well as slanting the shield up and down.

* * * * *